United States Patent [19]

Shiber

[11] Patent Number: 4,819,634

[45] Date of Patent: * Apr. 11, 1989

[54] ROTARY-CATHETER FOR ATHERECTOMY SYSTEM

[75] Inventor: Samuel Shiber, Mundelein, Ill.

[73] Assignee: Surgical Systems & Instruments, Mundelein, Ill.

[*] Notice: The portion of the term of this patent subsequent to Mar. 22, 2005 has been disclaimed.

[21] Appl. No.: 78,042

[22] Filed: Jul. 27, 1987

Related U.S. Application Data

[63] Continuation-in-part of Ser. No. 18,083, Feb. 24, 1987, which is a continuation-in-part of Ser. No. 874,546, Jun. 16, 1986, Pat. No. 4,732,154, which is a continuation-in-part of Ser. No. 609,846, May 14, 1984, abandoned.

[51] Int. Cl.$^4$ .............................................. A61B 17/32
[52] U.S. Cl. ...................................... 128/305; 604/95
[58] Field of Search ............... 128/305, 311, 656, 657, 128/658, 772; 604/22, 95, 282, 264

[56] References Cited

U.S. PATENT DOCUMENTS

| | | | |
|---|---|---|---|
| 3,749,086 | 7/1973 | Kline et al. | 604/95 |
| 3,773,034 | 11/1973 | Burns et al. | 604/95 |
| 4,020,829 | 5/1977 | Willson et al. | 604/95 |
| 4,368,730 | 1/1983 | Sharrock | 604/282 |
| 4,627,436 | 12/1986 | Leckrome | 128/303.1 |
| 4,676,249 | 6/1987 | Arenas et al. | 604/282 |
| 4,728,319 | 3/1988 | Masch | 128/305 |
| 4,729,763 | 3/1988 | Henrie | 128/305 |
| 4,732,154 | 3/1988 | Shiber | 128/305 |
| 4,737,153 | 4/1988 | Shimamura et al. | 604/282 |
| 4,749,376 | 6/1988 | Kensey | 128/305 |

*Primary Examiner*—Willis R. Wolfe
*Assistant Examiner*—M. Macy
*Attorney, Agent, or Firm*—Samuel Shiber

[57] ABSTRACT

A mechanical atherectomy system insertable into a human blood vessel over a flexible guide-wire for remotely cutting and removing an obstruction therein, having a diametrically stabilized torque transmitting flexible rotary-catheter equipped with a tubular-blade at its distal end and a motor connected to its proximal end.

22 Claims, 5 Drawing Sheets

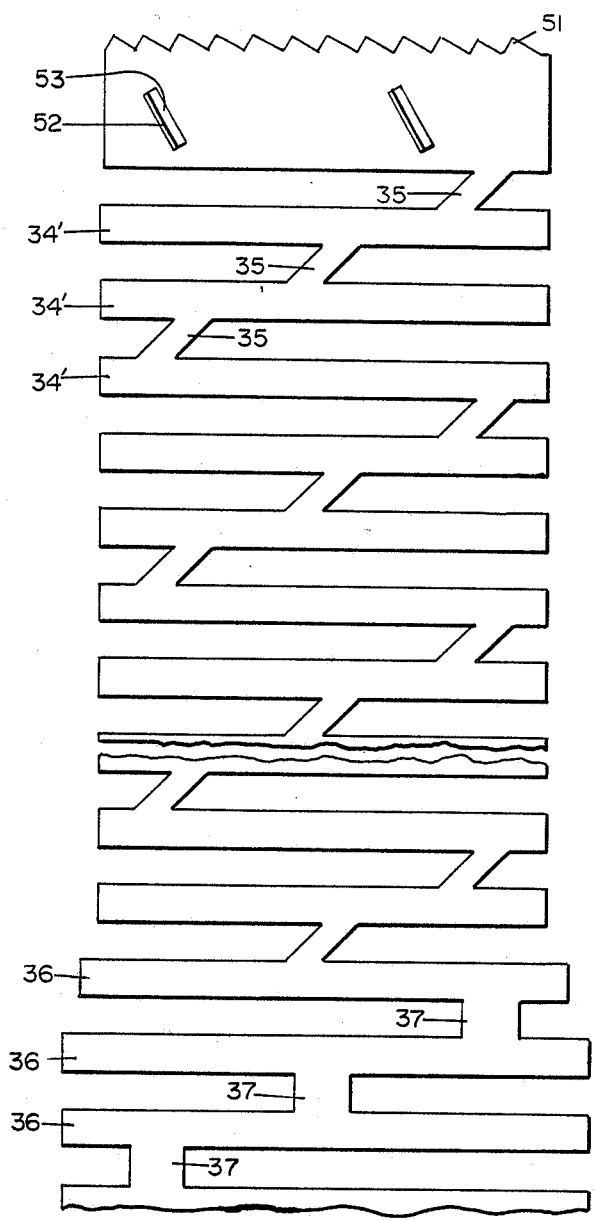
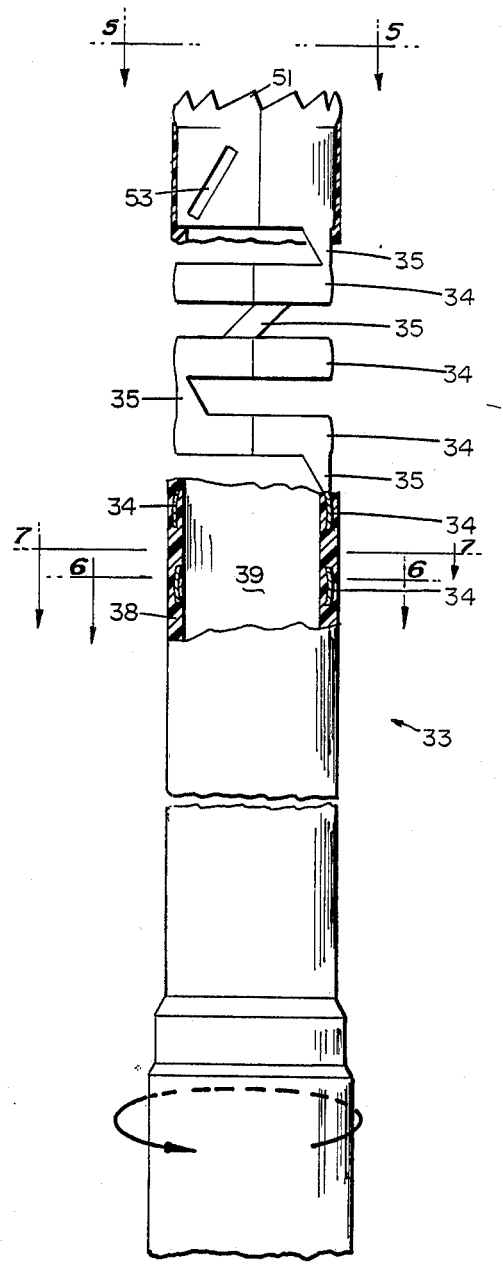
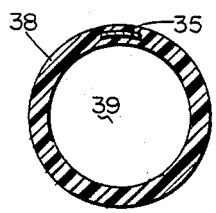
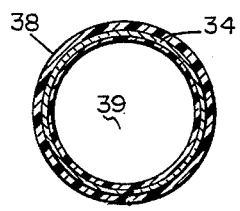
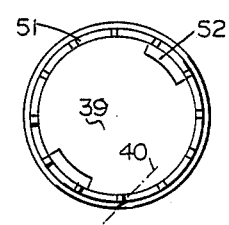
FIG. 4
FIG. 3
FIG. 7
FIG. 6
FIG. 5

ROTARY-CATHETER FOR ATHERECTOMY SYSTEM

CROSS REFERENCE TO OTHER APPLICATIONS

This application is a continuation-in-part of application Ser. No. 07/018083 filed on Feb. 24, 1987, still pending, which is a continuation-in-part of application Ser. No. 06/874,546 which was filed on June 16, 1986, now U.S. Pat. No. 4,732,154, which is a continuation-in-part of application Ser. No. 06.609,846 which was filed on May 14, 1984, now abandoned. The above prior applications are hereby being incorporated by reference.

BACKGROUND OF THE INVENTION

With age a large portion of the population develops arterial obstructions formed by fats, fibrous material and calcified deposits, resulting in a diminished blood circulation. These obstructions can induce blood clots which further diminish or block the blood flow. When this occurs in the coronary arteries serving the heart muscles it is referred to as a heart attack. Presently such obstructions are bypassed with a graft or they are treated by angioplasty using a catheter equipped with a balloon which is inserted, over a guide wire, into the obstruction through the arterial system and then inflated to dilate the obstruction's lumen. Problems with this treatment are that it injures the arterial wall and may burst it. In certain cases it is ineffective. it creates a rough lumen. It does not remove the obstructing material out of the vascular system and may even release obstruction material into the vascular system. Thus, angioplasty during a heart attach carries the risk of dislodging particles of the blood clot and allowing it to move down stream creating further, potentially critical, damage.

An objective of the present invention is to provide a flexible torque transmitting rotary catheter for a mechanical atheretomy system which can be percutaneously or intra-obstruction therein. The rotary-catheter is insertable and rotatable over a guide-wire and transmits rotation and torque to a blade affixed at its distal end from a motor affixed to its proximal end.

A further objective of the present invention is to provide a flexible rotary-catheter that would positively remove out of the human body the obstruction material, including blood clots if present, creates a smooth lumen, and would minimize injury to the blood vessel's wall.

A further objective of the invention is to provide a system that can be used actually during a heart attack to provide an immediate relief and a long term correction of the diseased arterial site.

The flexible rotary-catheter should be produceable in diameters down to around 1mm (millimeter) and a length of up to a meter to be able to reach and enter small and remote blood vessels. Preferably, the procedure using the mechanical atherectomy system would resemble angioplasty so that present skills of the medical staff can be utilized.

The rotary-catheter should be simultaneously flexible and capable of transmitting torque so that when it is introduced percutaneously to treat an obstruction in a remote artery, for example a coronary artery, if can assume a tortuous path of the vascular system including some sharp turns found in the coronary vascular system.

These and other objectives of the invention will become apparent from the following discussion and the accompanying drawings.

BRIEF DESCRIPTION OF THE FIGURES

FIG. 3 shows a partially sectioned view of a embodiment of a rotary-catheter.

FIG. 4 shows a skeleton member of the rotary-catheter of the first embodiment in its flat position before it has been rolled to form the intermittent tube shown in FIG. 3.

FIG. 5 shows an end view of a first embodiment viewed along line 5—5 marked on FIG. 3.

FIG. 6 shows a cross sectional view of the first embodiment as viewed along line 6—6 marked on FIG. 3.

FIG. 7 shows a cross sectional view of the first embodiment as viewed along line 7—7 marked on FIG. 3.

DETAILED DESCRIPTION OF THE DRAWINGS

Figures 1, 2:
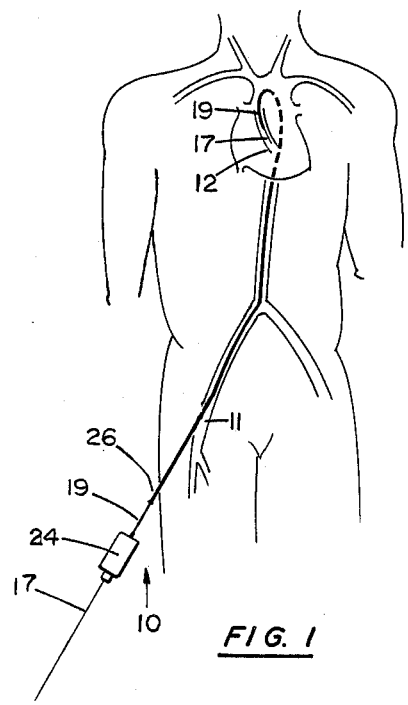
FIG. 1 shows a general view of a mechanical atheretomy system being inserted into an obstructed human coronary artery. The mechanical atherectomy system is introduced into the vascular system percutaneously at groin area and is snaked through the arterial system to reach the work site where the obstruction is about to be removed.
FIG. 2 shows a cross sectional view of the proximal and distal ends of the mechanical atherectomy system with its distal end inserted into an obstructed coronary artery. The general positioning of the parts corresponds to their position in FIG. 1. Due to space limitation the drawing sheets a segment or segments of the chanical atherectomy system and rotary catheter omitted and in FIG. 2 the mid section of the syst represented by a phantom line.
Figure 9:
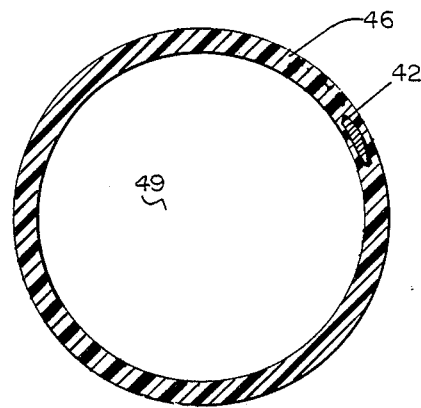
FIG. 9 shows a cross sectional view of the second embodiment as viewed along line 9—9 marked on FIG. 8.

FIG. 1 shows a general view of a mechanical atherectomy system 10 which is percutaneously introduced into a human femoral artery 11 at the groin area, and its distal end is snaked through the arterial system to reach a work site in a coronary artery 12.

FIG. 2 shows an enlarged cross sectional view of a proximal end 13 and of a distal end 14, of the system 10. The distal end is inserted into the diseased coronary artery 12 (same numbers are used to indicate same items throughout the FIGS.) containing a blood clot 15' seated on an atherosclerotic obstruction 15. The mid portion of the mechanical atherectomy system is represented by a phantom line 16.

The system 10 comprises a flexible guide-wire 17 having a section at its distal end shaped and an auger 18. The guide-wire is designed to be insertable through the human vascular system.

A flexible rotary-catheter 19 has a wall 20 defining a longitudinal channel 21. The catheter 19 is rotatable and slidable over the guide-wire 17. A tubular-blade 22 is mounted to the distal end of the rotary-catheter 19. The tubular-blade 22 defines a through-hole 23 forming with the channel 21 a continuous passageway for accepting the obstruction material ingested into the through-hole.

A motor 24 has a hollow tapered shaft 25 which couples to the proximal end of the flexible rotary-catheter through a matching tapered seat 30 for rotating it around the guide-wire 17.

A sleeve 26 introduces the rotary-catheter into the vascular system and may be extended to separate the arterial wall from the rotating catheter and to deliver contrast and/or irrigating fluid to the work site. The sleeve 26 may be formed to a desired shape and serve as a guiding-catheter and assist in guiding the system through the vascular system to the work site. A port 27 is provided to accept fluids for delivery through the sleeve's distal end and a seal 31 prevents the fluids from escaping out of the proximal end of the sleeve.

A rotary joint 28 has a port 29 which is connected through the hollow shaft 25 to the channel 21 and can be used for delivering fluids to the work site or for creating a negative pressure in the channel 21 to assist in drawing the obstruction material into it. The guide-wire slidabley passes through a close fitting hole formed at the end of the rotary joint 28.

FIG. 3 shows a first embodiment of a rotary-catheter 33 having means for diametricaly stabilizing the rotary-catheter while transmitting torque and being bent, as for example when cleaning an obstruction located in the coronary arteries illustrated in FIG. 2. The diametricaly stabilizing means is in the form of a series of hoop members 34 connected one to the other by the torque transmitting means in the form of strips 35. Collectively the hoops 34 and strips 35 form a skeleton of the rotary catheter on which a flexible plastic wall 38 is molded to define a channel 39.

FIG. 4 shows a shape cut out of a flat thin material such as stainless steel sheet, including horizontal strips 34' inter-connected by the inclined strips 35. At a later stage the horizontal strips 34' are folded and their ends bonded, or welded, to form the diametrically rigid hoops. As shown on FIG. 5 the ends of the strips 34' can be made to butt and bond along the inclined line 40 to avoid local double thickness of the hoop at the point of connection. The hoops rigidity can be enhanced by giving them a slight arced cross section as shown in FIG. 3. The thin strips 35 bend easily, but only in one direction, therefore they are phased at third of a circle intervals, as shown in FIG. 3 so that every three consecutive hoops act as a miniature universal-joint that can bend in any direction while transmitting rotation and torque.

During the manufacturing process, while the material is still flat, as shown in FIG. 4, it can be readily accessed with tools and dies, and teeth 51 and paddles 52 can be relatively easily fabricated onto it. The paddles can be formed by cutting a rectangular slot 53 along three of its sides and bending the material inwards around the fourth side which is left intact. The paddles 52 assist in pulling the obstruction material into the rotary-catheter 33 by turning the cut obstruction material that enter the through-hole around the stationary auger, and also be being inclined themselves the paddles operate as inclined planes to move the material into the rotary-catheter 33.

Since the torque that is transmitted through the rotary-catheter gradually increases with distance from its distal end due to additive frictional losses along the rotary-catheter, it is desirable to correspondingly increase the torque transmitting capacity of the rotary catheter. As shown in FIG. 4 horizontal strips 36 and vertical strips 37 have been made longer and wider, respectively, increasing the rotary-catheter diameter (not FIG. 3) and torque transmitting capacity (from hereon the small diameter and larger diameter catheter sections will be referred to as the neck and shaft sections, respectively).

Figure 8:
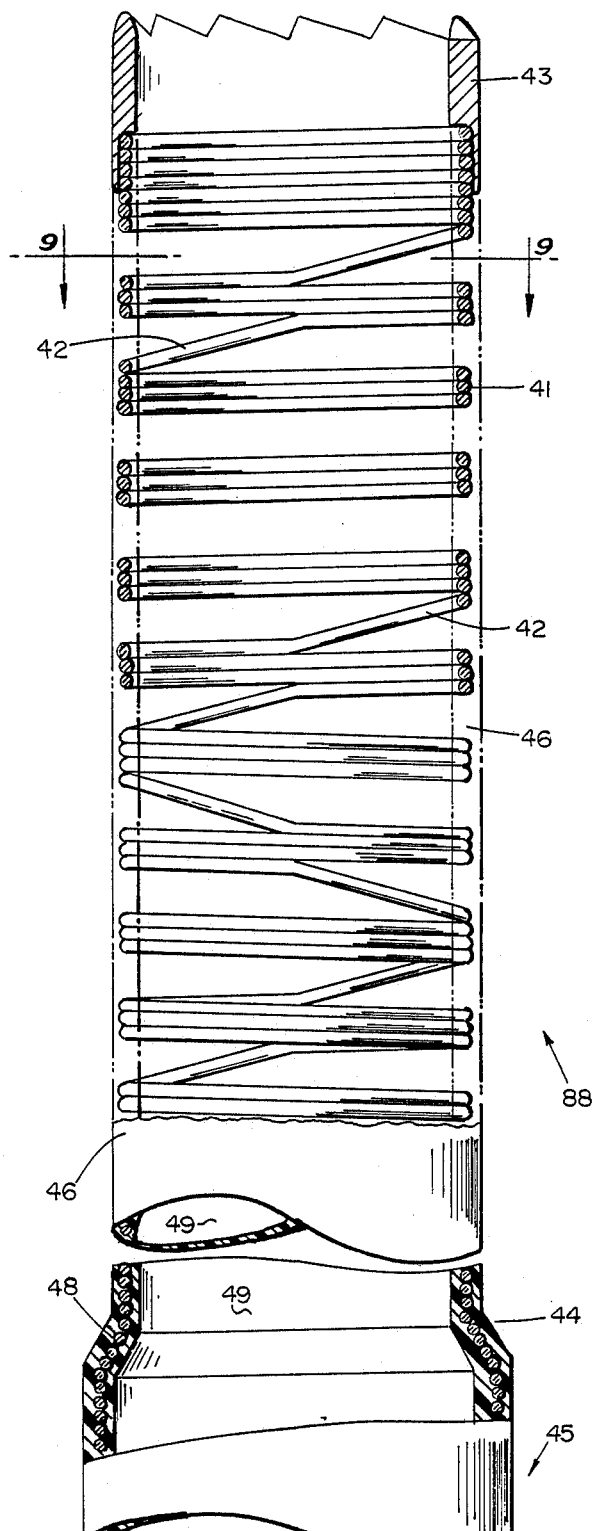
FIG. 8 shows a partially sectioned view of a second embodiment of a rotary-catheter.
Figure 11:
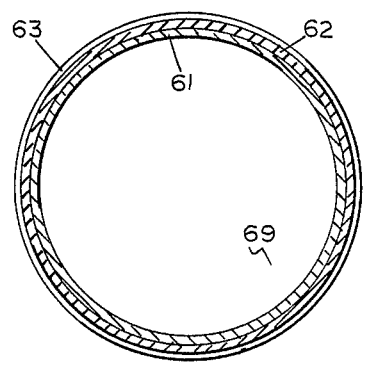
FIG. 11 shows a cross sectional view of the third embodiment as viewed along a line 11—11 marked on FIG. 10.
Figure 12:
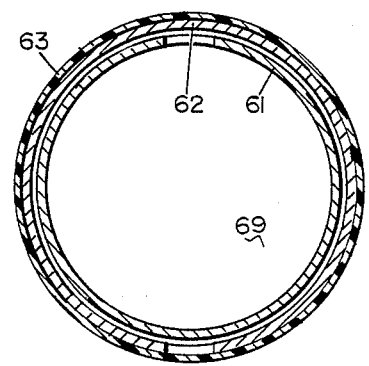
FIG. 12 shows a cross sectional view of the third embodiment as viewed along line 12—12 marked on FIG. 10.

FIG. 8 shows a second embodiment of a rotary-catheter 88 wherein the hoop members are few closely spaced windings 41 connected one to the other by a widely spaced partial winding 42. The closely spaced windings 41 can be brazed together to increase their diametrical stability. The widely spaced partial windings 42 serve to transmit torque from one hoop to the other. A tubular toothed blade 43 is brazed to the distal end of a skeleton (defined hereinafter). The rotary-catheter 88 comprises a neck section which extends from the blade 43 down to a point 44 at which point the rotary-catheter diameter increases to form a shaft section 45 with an increased torque transmitting capacity.

The windings 41, 42 and 48 (which is the continuation of the windings in the shaft section) form a skeleton over which a flexible plastic wall 46 is formed to complete the rotary-catheter's structure and define a channel 49 therein. The fact that the skeleton of the second embodiment is made of a continuous wire simplifies the handling and fabrication of the rotary catheter, however, notwithstanding this, individual hoop members can be used to stabilize the rotary catheter's diameter in which case the plastic wall itself transmits the torque.

Figure 10:
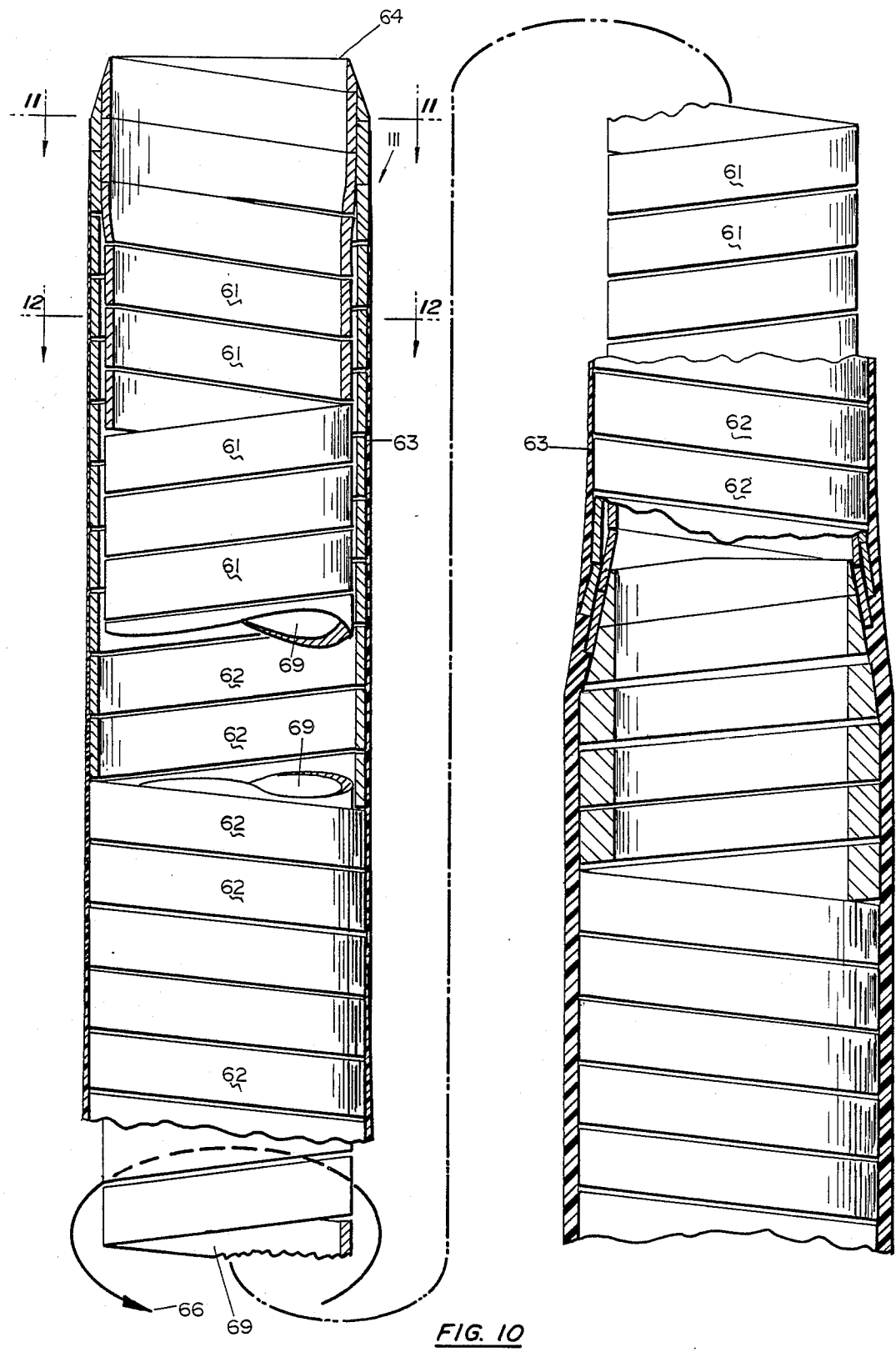
FIG. 10 shows a sectioned view of a third embodiment of the rotary-catheter.

FIG. 10 shows a third embodiment 111 of a rotary-catheter wherein the means for diametrically stabilizing and for transmitting torque comprise a helix 61 wound in the direction of rotation (which means that moving along the coils of the helix in the direction of rotation illustrated by arrow 66 on FIG. 10, while the helix is stationary, would cause advancing from the proximal end to the distal end). Such windings would tend to diametrically expand when the motor 24 drives the rotary-catheter 111 in the direction of the arrow 66, however, a second helix 62 wound in the counter-rotation direction tends to contract and thereby restrain the expansion of the first helix 61 and assist it in transmitting torque.

A flexible plastic wall 63 seals a channel 69 defined by the rotarycatheter 111 so that negative pressure or fluid introduced at its proximal end would reach its distal end. Alternatively, a thin plastic layer can be inlaid between the helixes to minimize friction between them.

When the helixes are made of flat ribbon material as shown in FIG. 10 they form a wall which does not seal fluids effectively but may be sufficient for the purposes of mechanically containing the cut obstruction particles without the benefit of the plastic layer 63. Therefore, if fluid conveyance or suction through the rotary catheter are not contemplated, the plastic wall 63 may be omitted to increase flexibility and decrease wall thickness of the rotary-catheter, and a thin slippery coating may be applied to the ribbons which are used to form the helixes, to minimize friction between the helixes and of the helixes with their surroundings.

A tubular blade 64 is made as an integral part of helixes 61 and 62, the last few coils of which are brazed together at their distal end and then sharpened.

Figure 13:
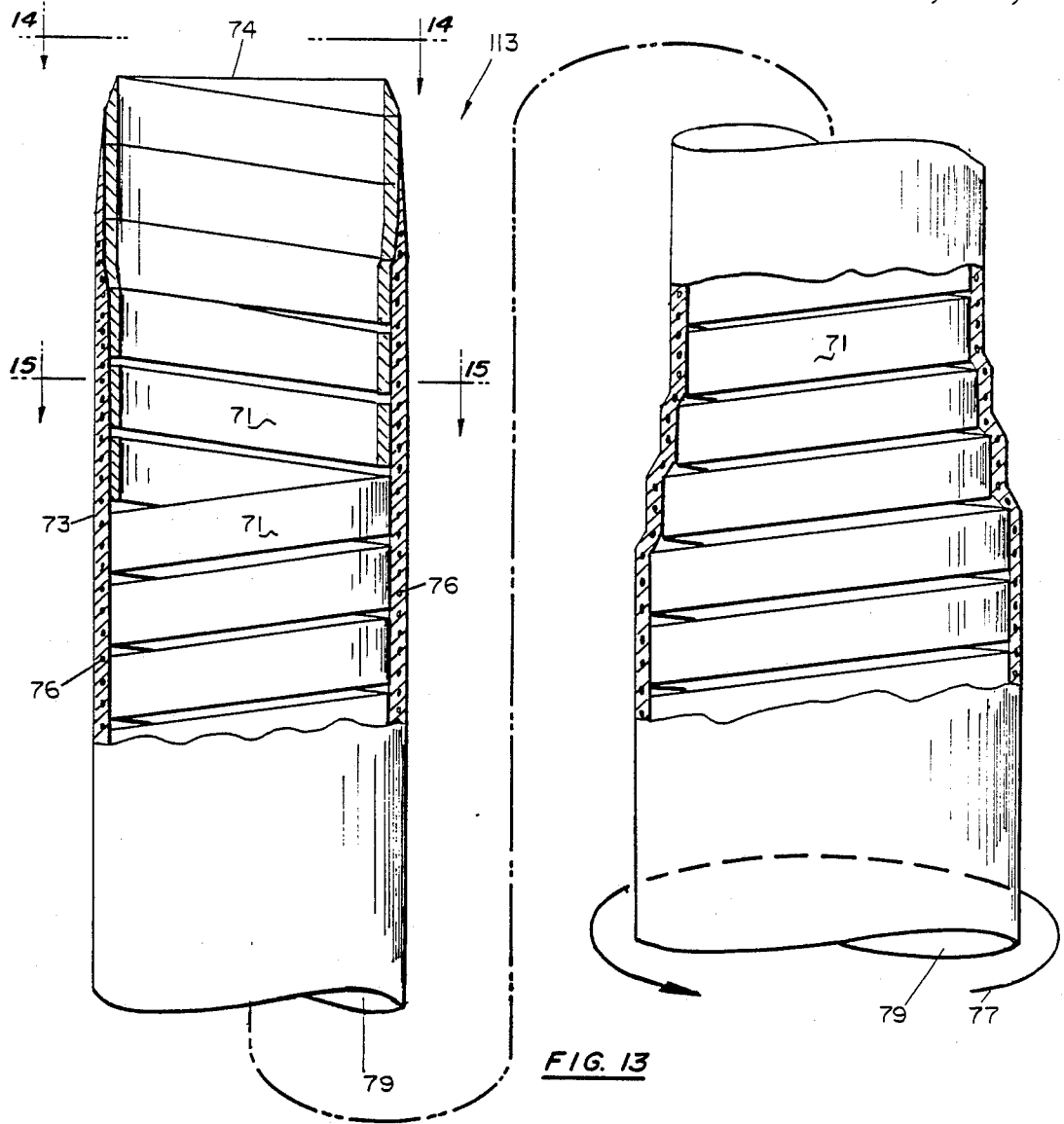
FIG. 13 shows a cross sectional view of a fourth embodiment of the rotary-catheter.
Figure 14:
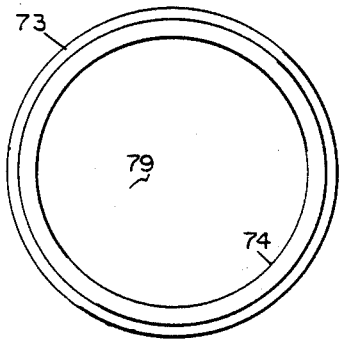
FIG. 14 shows an end view of the fourth embodiment as viewed along a line 14—14 marked on FIG. 13.
Figure 15:
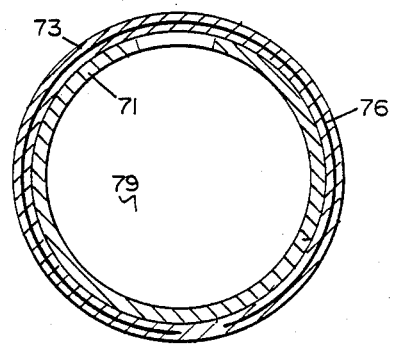
FIG. 15 shows a cross sectional view of the fourth embodiment as viewed along a line 15—15 marked on FIG. 13.

FIG. 13 shows a partially sectioned view of the fourth embodiment 113 of the rotary-catheter wherein the means for diametricaly stabilizing and for transmitting torque comprise a helix 71 would in the direction of rotation (which means that moving along the coils of the helix in the direction of rotation illustrated by arrow 66 on FIG. 10, while the helix is stationary, would cause advancing from the proximal end to the distal end). Such windings would tend to diametrically expand when the motor drives the rotary-catheter 113 in the direction of the arrow 77, however, an external restraining member in the form of a flexible wall 73 restrains such expansion (the wall's cross-sectional marking are standard, single line marking, not to obscure a cord 76 which is integrated therein). The wall restraining action is reinforced by peripheral retraining means 76 in the form of cord made of, for example, nylon or aramid fibers which restrain the diametrical expansion of the helix 71 but have little effect on the wall's ability to stretch along its longitudinal axis and therefore on its ability to bend as shown in FIGS. 1 and 2. The wall 73 defines a fluid worthy channel 79.

A tubular blade 74 is made as an integral part of the helix 71, the last few coils of which are brazed together at their distal end and then sharpened.

The present invention puts in the hand of the physician a method to immediately and effectively intervene in what is often referred to as a "heart attach" which is commonly caused by an obstruction made of a soft fresh blood clot formed on an atherosclerotic plaque which has developed for several years. Currently, the presence of the fresh blood clot, which has jelly like consistency, deters angioplasty since angioplasty may dislodge and release downstream some of the blood clot's material causing additional arterial occlusions possibly at points which would be more difficult to treat or points where no alternate blood supply exists (at the point of the original obstruction, being an "old" obstruction, alternate blood supply may have developed). Currently, several pharmacologic treatments are being tested that dissolve the blood clot, after which angioplasty may be performed, however because the present invention is effective in releasing and removing blood clots as well as atherosclerotic plaque it circumvents the delay and added risks that the pharmacologic treatment introduces, such as for example bleeding elsewhere.

The process for removing an obstruction made of a soft blood clot 15' formed on an atherosclerotic plaque from a blood vessel 12, comprises the following steps:

inserting into the blood vessel a guide-wire 17 and advancing it into the blood clot 15' which formed on the obstruction 15, inserting into the blood vessel, over the guide wire, the flexible rotary-catheter 19 having a proximal end 13 and a distal end 14 with a tubular-blade 22 affixed thereto, advancing the distal end 14 to mechanically engage and unseat the blood clot 15' while applying suction to port 29 to suck the blood clot 15' into the through-hole 23, advancing the tubular-blade 22 to rotatably engage and peripherally cut the atherosclerotic plaque of the obstruction 15, removing the blood clot, the atherosclerotic plaque and the flexible rotary-catheter 19 out of the blood vessel 12.

It should be noted that a tubular-blade is efficient and requires less energy input, in comparison to blades used in alternative mechanical systems which pulverize the obstruction material. To illustrate this point, when the tubular-blade 22 peripherally cuts and extracts an obstruction with an outside diameter of 3 mm, an inside diameter (lumen) of 1mm and a length of 10 mm the area that the tubular-blade 22 has to cut through is approximately 100 square mm. If a conventional blade, for example as shown in U.S. Pat. No. 4,445,509 by Auth, is used to break the same obstruction to shavings measuring 0.1mm by 0.1mm by 0.1 mm the area that the conventional blade would have had to cut through is approximately 3800 square mm, and this much larger area requires a much larger energy input to the blade increasing the probability of traumatizing the artery. Further, the hollow construction of the flexible rotary-catheter enables it to swallow the obstruction material as it is being cut for efficient removal thereof.

While the present invention has been illustrated by a limited number of embodiments, it should be understood that various modifications and substitutions may be made without departing from the spirit of the invention or the scope of the claims.

I claim:

1. A mechanical atherectomy system insertable into a human blood vessel for remotely cutting and removing an obstruction therein, comprising in combination:

a flexible guide-wire insertable into said blood vessel, a flexible rotary-catheter defining a channel and having distal and proximal ends, said flexible rotary-catheter being rotatably disposed and slidable over said guide-wire, a tubular-blade mounted to said distal end, said tubular-blade having a through-hole forming with said channel a continuous passage for passing obstruction material ingested into said through-hole, into said flexible rotary-catheter, coupling means at said proximal end of said flexible rotary-catheter for rotating said flexible rotary-catheter and said tubular-blade around said guide-wire, means for diametricaly stabilizing and means for transmitting torque being incorporated in said flexible rotary-catheter.

2. A mechanical atherectomy system as in claim 1, wherein said means for diametricaly stabilizing said rotary-catheter comprise a series of hoop members connected one to the other by said torque transmitting means.

3. A mechanical atherectomy system as claim 2, wherein said hoop members are rolled strips connected one to the other by strips.

4. A mechanical atherectomy system as in claim 2, wherein said hoop members are closely spaced windings connected one to the other by a widely spaced winding.

5. A mechanical atherectomy system as in claim 1, wherein said means for diametricaly stabilizing comprise a helix wound in the direction of rotation, an external member restraining the expansion of said helix, said helix carrying at least part of the torque transmitted through said flexible rotary-catheter.

6. A mechanical atherectomy system as in claim 5, wherein said external restraining member comprise a helix wound in the counter rotation direction.

7. A mechanical atherectomy system as claim 5, wherein said external retraining member comprise a flexible wall.

8. A mechanical atherectomy system as in claim 7, wherein said flexible wall contains peripheral restraining means.

9. A mechanical atherectomy system as claim 1, wherein said tubular blade is an integral part of said means for diametricaly stabilizing said flexible rotary-catheter.

10. A mechanical atherectomy system as in claim 1, wherein said tubular blade is an integral part of said means for transmitting torque.

11. A process for removing from a human blood vessel a soft blood clot, comprising the following steps:
   inserting into said blood vessel a guide-wire and advancing it into said blood clot,
   inserting into said blood vessel, over said guide wire, a flexible rotary-catheter having a distal and proximal ends, advancing said distal end to mechanically engage and unseat said blood clot while applying suction to said proximal end to such said blood clot into said distal end,
   removing said blood clot and said catheter out of said blood vessel.

12. A process as in claim 11, wherein, at least a portion of said guide-wire is shaped as an auger.

13. A process for removing from a human blood vessel an obstruction made of a soft blood clot formed on an atherosclerotic plaque, comprising the following steps:
   inserting into said blood vessel a guide-wire and advancing it into said blood clot,
   inserting into said blood vessel, over said guide wire, a flexible rotary-catheter having a proximal end and distal end with a tubular blade affixed to said distal end,
   advancing said distal end to mechanically engage and unseat said blood clot while applying suction to said proximal end to suck said blood clot into said distal end,
   rotating and advancing said tubular blade to peripherally cut and swallow said atherosclerotic plaque,
   removing said blood clot, said atherosclerotic plaque and said catheter out of said blood vessel.

14. A process as in claim 13, wherein, at least a portion of said guide-wire is shaped as an auger.

15. A mechanical atherectomy system insertable into a human blood vessel for remotely cutting and removing an obstruction therein, comprising in combination:
   a flexible guide-wire insertable into said blood vessel,
   a flexible rotary-catheter defining a channel and having distal and proximal ends, said flexible rotary-catheter being rotatably disposed and slidable over said guide-wire, a tubular-blade mounted to said distal end, said tubular-blade having a through-hole forming with said channel an inner wall which defines a continuous passage for accepting ingested obstruction,
   said inner wall having inclined plane means which assist in pulling the obstruction material into the continuous passage,
   coupling means at said proximal end of said flexible rotary-catheter for rotating said flexible rotary-catheter and said tubular-blade around said guide-wire.

16. A mechanical atherectomy system as in claim 15, wherein said flexible rotary-catheter is rotatebly disposed in a sleeve.

17. A mechanical atheretomy system as in claim 15, wherein said flexible rotary-catheter comprise a helix wound in the direction of rotation.

18. a mechanic atherectomy system as in claim 17, wherein said flexible rotary-catheter is rotatebly disposed in a sleeve.

19. A mechanical atherectomy system as in claim 17, wherein a restraining member surrounds said helix and restrains its diametrical expansion.

20. A mechanical atherectomy system as in claim 19, wherein said restraining member comprise a helix wound in the counter rotation direction.

21. A mechanical atherectomy system as in claim 19, wherein said restraining member comprise a flexible wall.

22. A mechanical atherectomy system as in claim 21, wherein said flexible wall contains peripheral restraining means.

* * * * *